(12) United States Patent
He et al.

(10) Patent No.: US 9,116,042 B1
(45) Date of Patent: Aug. 25, 2015

(54) CAVITY RING DOWN SPECTROSCOPY USING MEASURED BACKWARD MODE DATA

(71) Applicant: Picarro, Inc., Santa Clara, CA (US)

(72) Inventors: Yonggang He, Union City, CA (US); Sze Meng Tan, Sunnyvale, CA (US); Alejandro Dario Farinas, Mountain View, CA (US)

(73) Assignee: Picarro, Inc., Santa Clara, CA (US)

( * ) Notice: Subject to any disclaimer, the term of this patent is extended or adjusted under 35 U.S.C. 154(b) by 0 days.

(21) Appl. No.: 14/015,791

(22) Filed: Aug. 30, 2013

Related U.S. Application Data

(63) Continuation-in-part of application No. 13/065,270, filed on Mar. 18, 2011, now Pat. No. 8,537,362.

(51) Int. Cl.
 *G01J 3/42* (2006.01)
(52) U.S. Cl.
 CPC .......................................... *G01J 3/42* (2013.01)
(58) Field of Classification Search
 USPC ................................................. 356/432–444
 See application file for complete search history.

(56) References Cited

U.S. PATENT DOCUMENTS

| | | | | |
|---|---|---|---|---|
| 5,528,040 | A * | 6/1996 | Lehmann ....................... | 250/343 |
| 7,012,696 | B2 * | 3/2006 | Orr et al. ......................... | 356/454 |
| 7,154,595 | B2 * | 12/2006 | Paldus et al. ..................... | 356/73 |
| 7,855,788 | B2 * | 12/2010 | Ito et al. ......................... | 356/451 |
| 8,537,362 | B2 * | 9/2013 | He et al. ......................... | 356/437 |
| 8,642,982 | B2 * | 2/2014 | Plusquellic et al. ....... | 250/493.1 |
| 2013/0228688 | A1 * | 9/2013 | Plusquellic et al. ..... | 250/339.06 |

OTHER PUBLICATIONS

Busch et al. "Introduction to Cavity-Ringdown Spectroscopy", 1999, pp. 7-19, American Chemical Society.

* cited by examiner

*Primary Examiner* — Kara E Geisel
*Assistant Examiner* — Jarreas C Underwood
(74) *Attorney, Agent, or Firm* — Lumen Patent Firm

(57) ABSTRACT

In cavity ring-down spectroscopy (CRDS), scattering into the backward mode of a traveling wave ring-down cavity can degrade conventional CRDS performance. We have found that this performance degradation can be alleviated by measuring the backward mode signal emitted from the ring-down cavity, and using this signal to improve the processing for extracting ring-down times from the measured data. For example, fitting an exponential to the sum of the intensities of the forward and backward signals often provides substantially better results for the ring-down time than fitting an exponential to the forward signal alone. Other possibilities include extracting cavity eigenmode signals from the forward and backward signals and performing separate exponential fits to the eigenmode signals. An optical circulator can be used to facilitate measurement of the backward mode signal.

15 Claims, 11 Drawing Sheets

CAVITY RING DOWN SPECTROSCOPY USING MEASURED BACKWARD MODE DATA

CROSS REFERENCE TO RELATED APPLICATIONS

This application is a continuation in part of U.S. patent application Ser. No. 13/065,270, filed on Mar. 18, 2011, and hereby incorporated by reference in its entirety.

FIELD OF THE INVENTION

This invention relates to cavity ring-down spectroscopy.

BACKGROUND

Cavity ring-down spectroscopy (CRDS) is an analytical technique where optical radiation emitted from a passive optical cavity is measured as a function of time. The decay rate of this emitted radiation is related to the loss in the cavity (lower loss leads to slower decay). Typically, an exponential decay is fitted to the measured radiation intensity to determine the ring-down time. Absorption caused by an analyte in the cavity affects the ring-down time, so measuring the ring-down time amounts to a highly sensitive form of absorption spectroscopy. The resulting CRDS instruments are widely applicable to various analysis applications, especially in cases requiring ultra-high sensitivity (e.g., part per billion level).

Ideally, only a single cavity mode is relevant during a ring-down measurement, with all other modes having negligible amplitude. The reason for this is that intracavity loss will tend to have a different effect on the decay rates of each of the cavity modes, so a clean single-exponential decay can only be obtained for single-mode excitation.

The cavity in a CRDS instrument can be either a standing wave cavity or a traveling wave cavity. A typical example of a standing wave cavity is a two-mirror cavity where a round trip of the cavity mode entails propagating on the path between the two mirrors once in each direction. A typical example of a traveling wave cavity is a three mirror ring cavity, where a round trip of the cavity mode entails propagating on a path around the ring cavity (e.g., in a clockwise or counter clockwise direction).

In CRDS using a traveling wave cavity, one typically distinguishes between the forward mode, which is driven by the optical source of the CRDS instrument, and the backward mode which is at the same frequency as the forward mode, but propagates in the opposite direction. For example, if the forward mode propagates clockwise around a ring cavity, the corresponding backward mode propagates counter clockwise, and vice versa.

Ideally, the amplitude of the backward mode would be zero, so this mode is usually neglected in conventional accounts of CRDS operation. However, there is some consideration of the backward mode in the art. In U.S. Pat. No. 7,646,485, two ideas are considered. The first idea relates to performing more complicated curve fitting than a simple exponential to mitigate the effect of backward mode artifacts on CRDS results. The second idea relates to measuring excitation of the backward mode by a source aligned to nominally excite only the forward mode to provide an indication of the quality of the cavity alignment. Adjustment of the cavity alignment during assembly to minimize the measured excitation of the backward mode can be helpful for improving the cavity alignment of the finished instrument.

SUMMARY

In this work, some problems that can arise in connection with excitation of the backward mode of a traveling wave cavity during ring-down measurements are identified. Several approaches are also presented for alleviating these problems. To better appreciate the present approach, it is helpful to consider CRDS operation in greater detail.

In cavity ring-down spectroscopy, the optical absorption of a sample within an optical cavity is obtained by fitting an exponential to the decaying intensity of light emanating from the cavity after the (monochromatic) excitation has been turned off. The exponential decay is characteristic of the damping of a single mode. With a traveling wave cavity, a pair of degenerate counter-propagating modes is present for each resonant frequency. Ideally, only one of these modes is excited by the source but imperfections (such as scattering) can produce a weak coupling between the primary (ring-down) mode and the backscattered mode.

During a ring-down, the mode coupling causes periodic exchange of energy between the modes, in addition to the decay. If the intensity of the primary mode only is monitored, the waveform is no longer precisely exponential, leading to a bias in the ring-down time estimate which depends on the degree of excitation and relative phase of the backscattered mode. Since the excitation varies from shot to shot, depending on the precise moment at which the source is turned off, one effect of neglecting the backscattered mode is an increase in the noise or variability of successive ring-down time measurements.

A second effect is found when a spectrum of the cavity loss is measured. Depending on the positions of the scatterers which couple the forward and backward modes, interference effects can cause the effective coupling strength to depend on the frequency of the excitation. The bias and noise introduced by fitting the forward mode alone can thus be frequency dependent, thereby confusing the interpretation of spectra. In the case of a 3-mirror ring resonator, if scatterers are on different mirrors, then the frequency dependence appears as a modulation of the resonator baseline optical loss and noise with a period corresponding to the reciprocal of twice the spatial separation (the distance between the mirrors) modulo the resonator free spectral range.

By solving the equations for the coupled modes during a ring-down, it is found that under the assumption of fixed point-like weakly scattering centers, the sum of the intensities of both modes (i.e., forward and backward) does decay approximately exponentially, although the intensities of the individual forward and backward modes are non-exponential. For more general scattering, for example by nearly-resonant atoms, this is no longer precisely true, but it remains a good approximation if the absorption is weak. Thus, by performing an exponential fit to the sum of intensities of both modes during a ring-down, the above-identified deleterious effects can be reduced.

More specifically, a CRDS instrument having a traveling wave cavity is considered. The traveling wave cavity has forward and backward modes that propagate in opposite directions in the cavity. The instrument includes an optical source capable of providing optical radiation to the cavity. It also includes an optical detection unit that receives forward mode and backward mode optical signals from the cavity and provides one or more electrical detector signals. A processor (e.g., a data acquisition system) receives the electrical detector signals and provides a cavity loss derived from the electrical signals as an output.

As seen in greater detail below, there are at least three configurations for the optical detection unit. The first configuration has two separate detectors, one for the forward mode and the other for the backward mode. The second configuration has a single detector at which both the forward and backward optical signals are detected to provide a sum intensity signal. In the third configuration, an optical interferometer is added to the detector unit to transform the forward and backward mode optical signals to cavity eigenmode signals (e.g., sine and cosine signals). The third configuration can have one or two detectors, depending on whether or not both interferometer output ports are detected. The path length difference of the interferometer is preferably about a wavelength or less, where the wavelength is set by the optical source and can be any wavelength at which CRDS is possible.

Optionally, an anti-reflection unit can be added to prevent reflection by the detector(s) from reaching the cavity. Such anti-reflection can be provided by Faraday isolator(s), or by a less costly combination of polarizer and quarter-wave plate if the detector reflection and/or scattering preserves polarization.

As indicated above, some embodiments relate to forming a sum intensity signal of the forward and backward signals, and to performing an exponential fit to the sum intensity signal to determine the ring-down time (i.e., the cavity loss). If separate detectors are used for the forward and backward optical signals, the summing is performed electrically. Analog and/or digital electronics can be used for this operation. One option is to provide the detector photocurrents to the summing junction of a trans-impedance amplifier.

Other embodiments relate to deriving cavity eigenmode signals from the forward and backward mode optical signals. If this is done, more extensive data processing can be performed. For example, separate exponential fits can be performed for each of the cavity eigenmode signals to improve the determination of the ring-down time.

Further embodiments make use of an optical circulator to separate source radiation from the backward mode signal.

DETAILED DESCRIPTION

Figure 1:
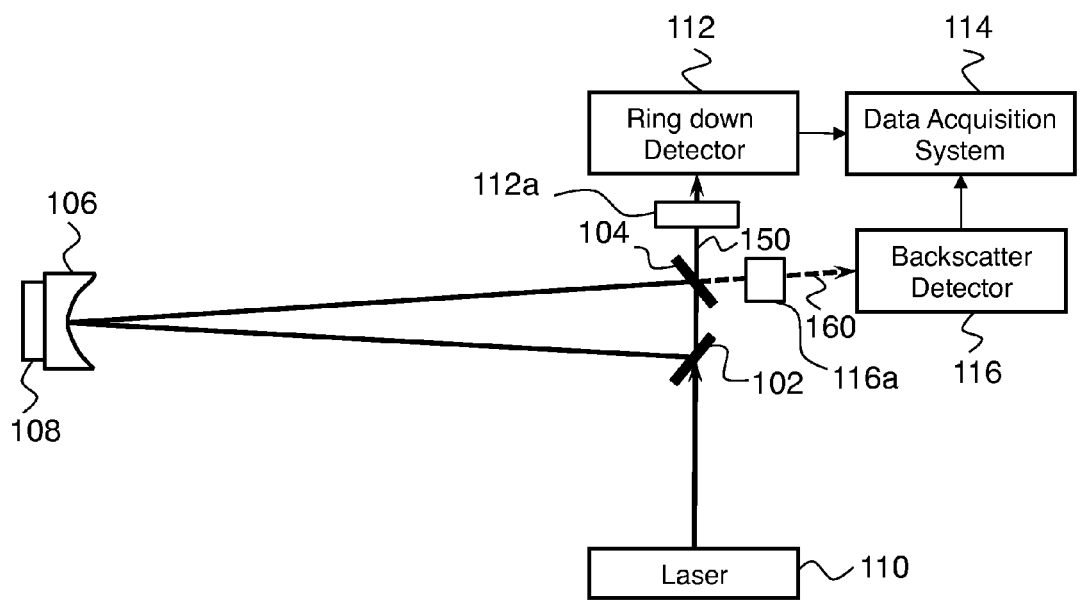
FIG. 1 shows a first embodiment of the invention.

A first embodiment of the invention involves using two separate photodiodes to monitor the intensity of light in the forward and backward modes. For a ring cavity, these may both be conveniently accessed from the output mirror as illustrated schematically in FIG. 1. Here a ring cavity is formed by mirrors 102, 104, and 106. A mechanical transducer 108 (e.g., a PZT transducer) is connected to mirror 106 such that its position can be altered under electrical control, thereby providing the capability to adjust cavity mode frequencies as needed for CRDS operation. A source 110 provides radiation to the cavity, and it can be seen from the figure that the forward mode propagates counter clockwise in the cavity of this example. Ring-down detector 112 receives a signal 150 from the cavity, and it is apparent from the geometry of FIG. 1 that signal 150 is a forward mode signal. Similarly, it is apparent that backscatter detector 116 receives a backward mode signal 160 from the cavity. Light emitted from the cavity follows path 160 only if it is propagating clockwise in the cavity (i.e., only if it is the backward mode). Detectors 112 and 116 are connected to a data acquisition system 114.

The photocurrents may be individually amplified and the outputs summed using an analog network or digitally after analog-to-digital conversion. In an alternative realization, the photocurrents may be connected to the summing junction of a single trans-impedance amplifier. It is important that the two channels be matched as well as possible, and for the outgoing beams to be well-captured by the detectors in order to realize the full benefits of the method.

Optionally, optical isolation can be provided by isolators 112a and/or 116a to prevent reflections by detectors 112 and 116 from propagating to the optical cavity. An optical isolator placed on either or both beams 150 and 160 incident on the detectors will also serve to prevent accidental coupling of the forward and backward beams to each other outside the cavity. If the detector reflection and scattering preserves polarization, then a cheaper alternative to an isolator with Faraday rotation is a combination of linear polarizer and quarter-wave plate. The polarizer is aligned to the input beam polarization, and then the quarter-wave plate transforms the beam to circular polarization, incident on the detector. Any reflection passes back through the quarter-wave plate, which transforms to linear polarization perpendicular to the polarizer, which then blocks it.

Figure 2A:
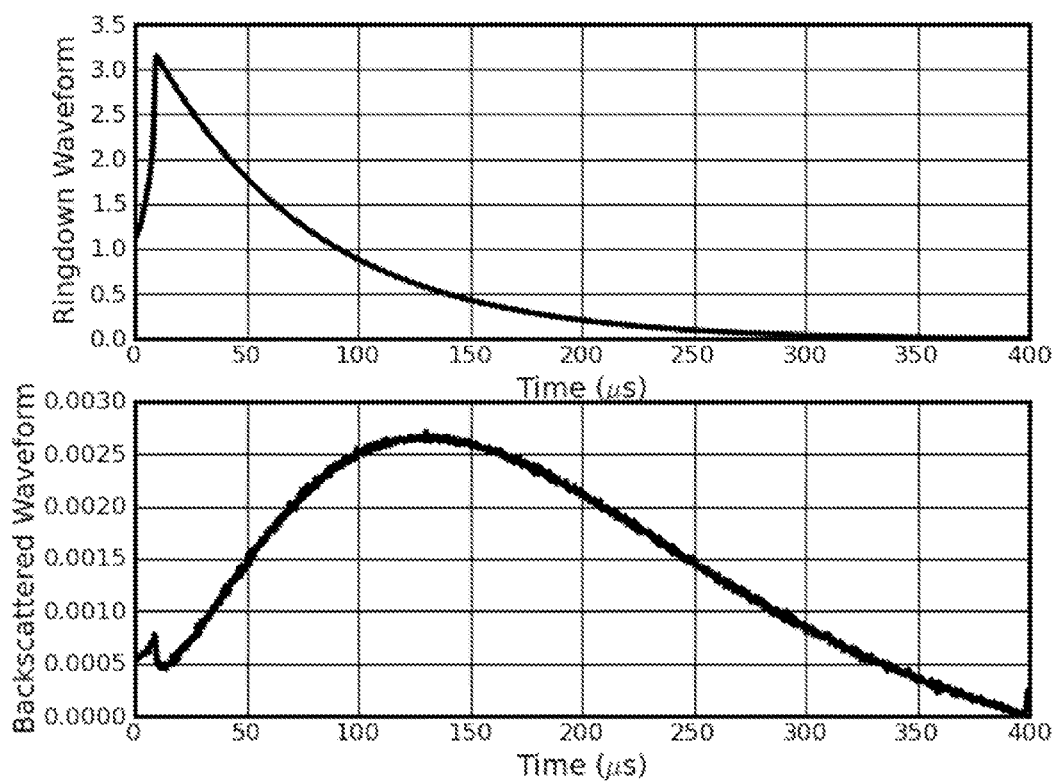
FIG. 2a shows measured ring-down curves for the forward and backward modes in an experiment (first embodiment).
Figure 2B:
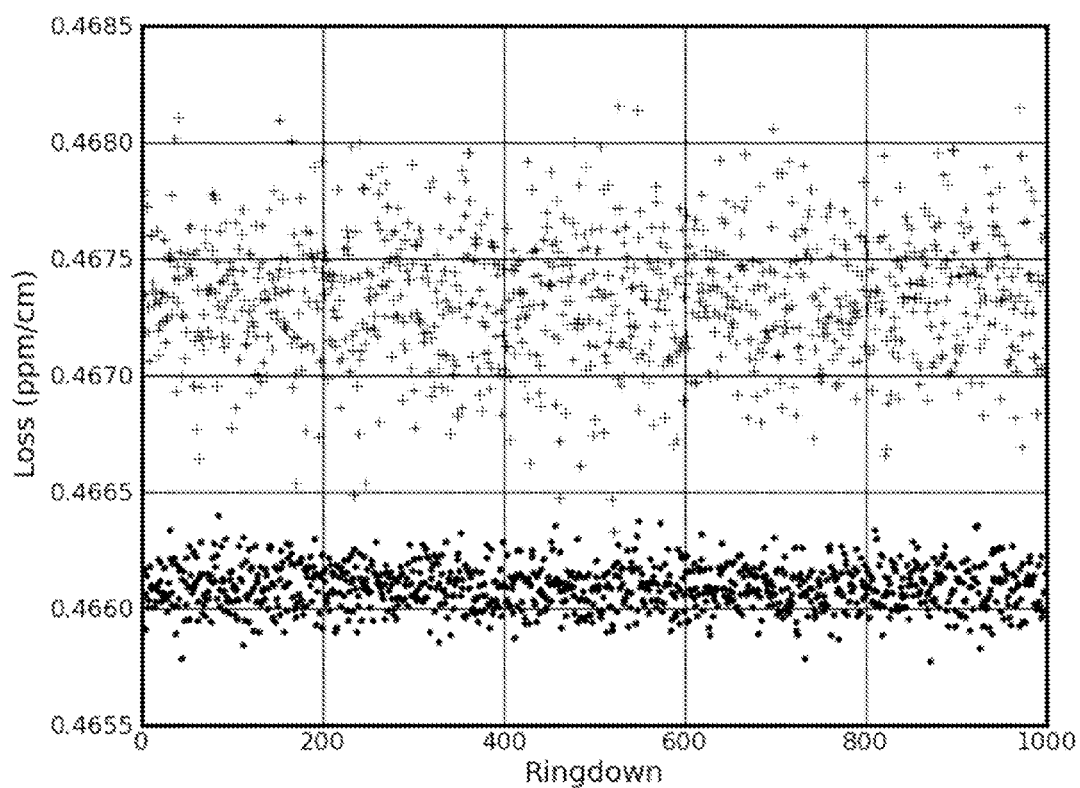
FIG. 2b shows a scatter plot of measured cavity losses with and without corrections according to the present principles (first embodiment).

In FIG. 2a, forward (top plot) and backward (bottom plot) intensities are shown for an average of 1000 ring-down shots collected with light of a single frequency. The shapes of these waveforms correspond closely to those predicted by the coupled mode equations for point scatterers. The results of performing exponential fitting on the ring-down intensity alone (crosses) and on the sum of both intensities (circles) are shown in FIG. 2b. In this experiment, the fractional variability in the cavity loss (expressed as a percentage) has been reduced almost by a factor of three, from 0.060% to 0.022%.

Figure 3:
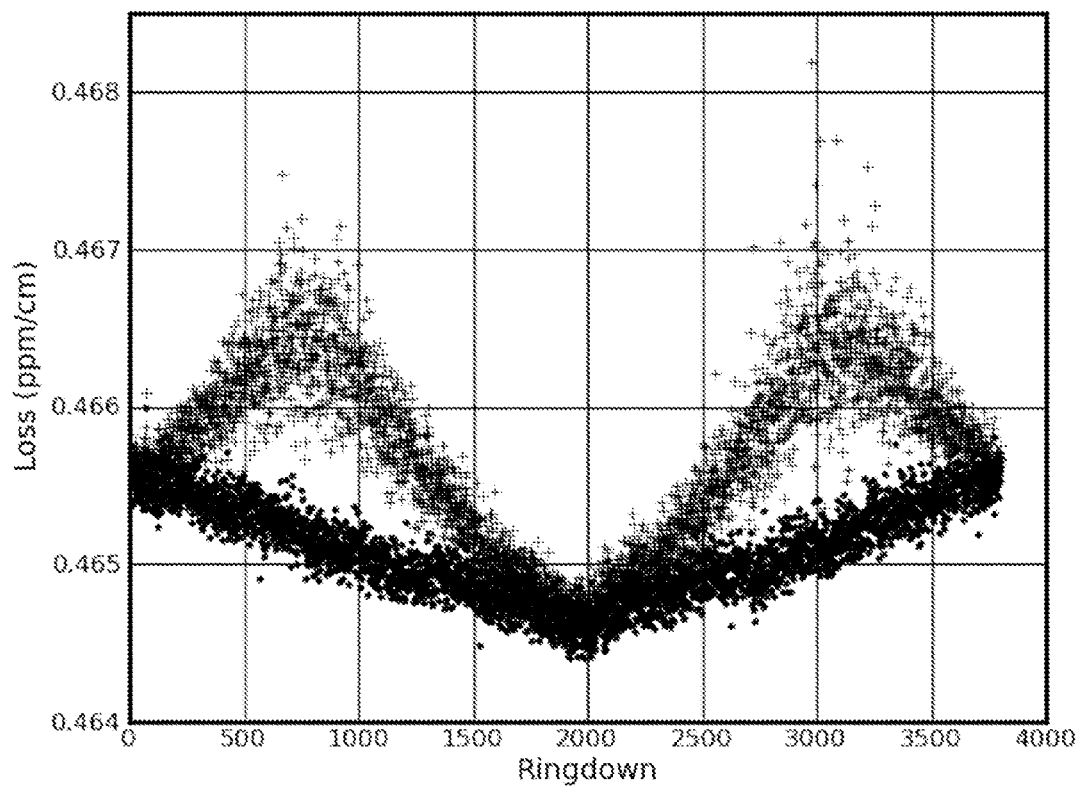
FIG. 3 shows a scatter plot of measured cavity losses with and without corrections according to the present principles for a wavelength scan (first embodiment).

In FIG. 3, the excitation frequency is slowly swept from 6251 cm$^{-1}$ to 6252 cm$^{-1}$ and back to 6251 cm$^{-1}$ while collecting ring-downs. A small change in the cavity loss is expected, due to the frequency dependence of the mirror coatings, and the change is expected to be approximately linear since the sweep is very narrow compared with the coating bandwidth. The results from fitting the ring-down mode alone (crosses) show an unexpected peak in the loss in the interior of the sweep. This is an example of the frequency dependence of the baseline and noise caused by the interference between (at least) two scatterers. On the other hand, fitting the sum of the mode intensities (circles) shows the expected smooth change with frequency. The noise on the former spectrum varies with frequency by a factor of more than three, while that on the latter is essentially constant.

A second embodiment of this invention involves using a single detector for both the forward and backward modes. Two fold mirrors can be added to a configuration as in FIG. 1 to reflect transmitted backward waves so that the photon energy of both the forward and the backward waves can be combined and detected by the same photodiode.

Figure 4:
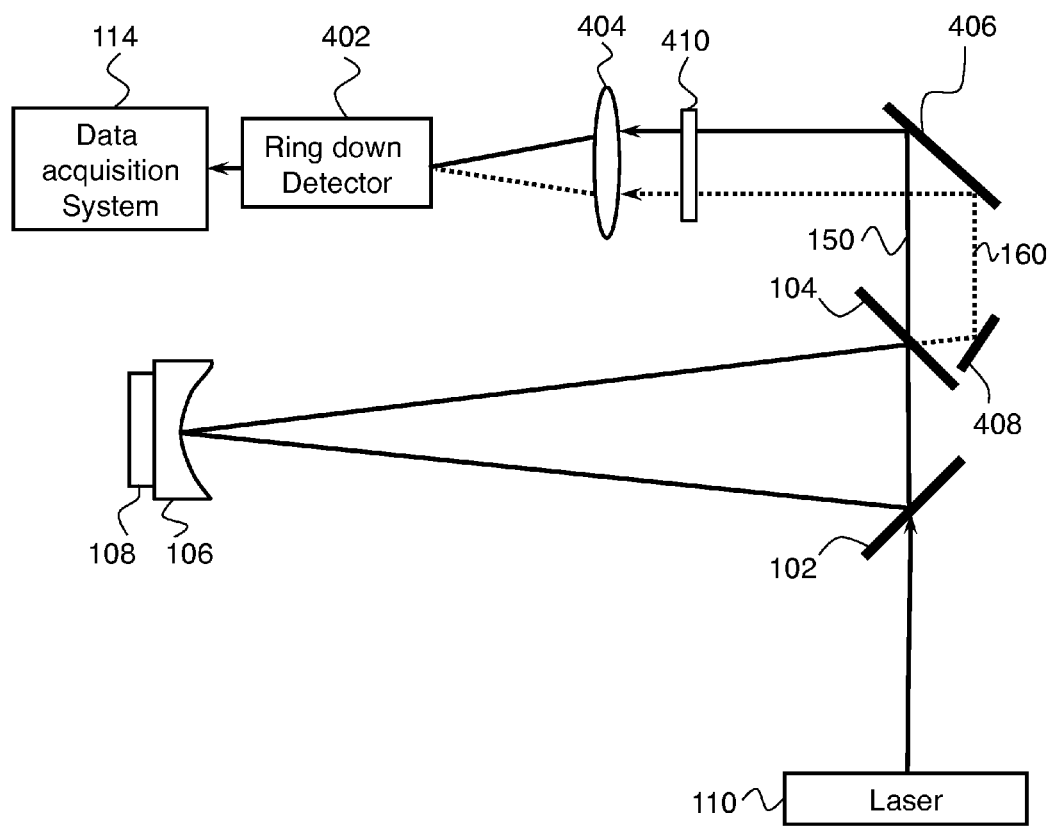
FIG. 4 shows a second embodiment of the invention.

FIG. 4 shows an example of this approach. The modification to the system of FIG. 1 includes two additional fold mirrors 406 and 408. These additional mirrors reflect the backward signal 160 (dotted trace) into the same ring-down detector 402 that detects the forward signal 150. The two added mirrors are aligned so that the backward and forward beams are nearly parallel to each other. As a consequence only one focus lens 404 is needed to collect both beams to the ring-down detector 402. Optionally, isolation can be provided by an isolator 410, in a similar manner as described in connection with FIG. 1. The system of FIG. 4 is an illustrative example, and practice of the invention does not depend critically on details of the fold mirrors or the lens, such as their number and arrangement, provided that both forward and backward signals reach the same detector. It is also not critical whether or not the two beams interfere at the detector, provided that the detector is linear over the relevant optical intensity range.

Figure 5:
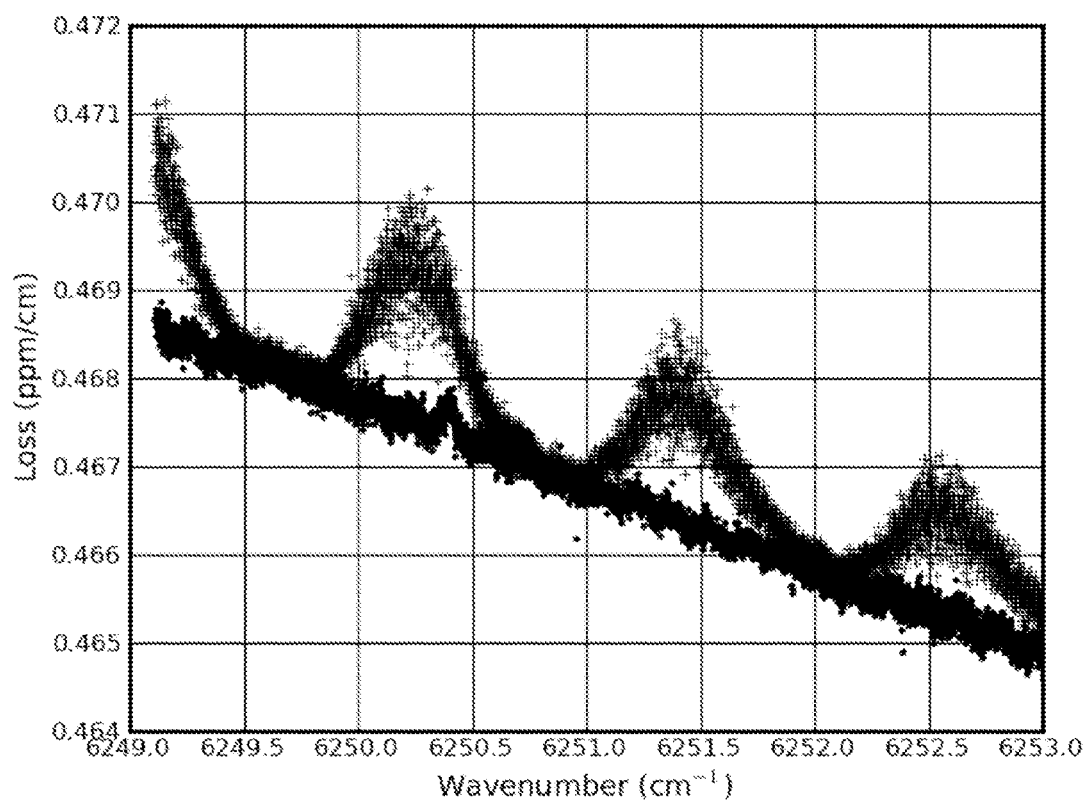
FIG. 5 shows a scatter plot of measured cavity losses with and without corrections according to the present principles for a wavelength scan (second embodiment).

In FIG. 5, the laser wavelength is swept between 6249 cm$^{-1}$ and 6253 cm$^{-1}$ while collecting ring-downs. The overall change in loss is due to the frequency dependence of the mirror coatings, and the change is expected to be approximately linear since the sweep is very narrow compared with the coating bandwidth. The trace marked with crosses shows the frequency dependence of the loss before the modification was implemented. A ripple with a period of ~1.2 wavenumber is clearly seen. The noise on the spectrum varies with frequency by a factor of more than three. With the present approach, this ripple is almost completely removed by detecting the combined photon energy from both the forward and backward waves at a single detector (trace marked with circles). In addition the noise, reduced by a factor of ~3, is essentially constant throughout the whole scan region.

Figure 6:
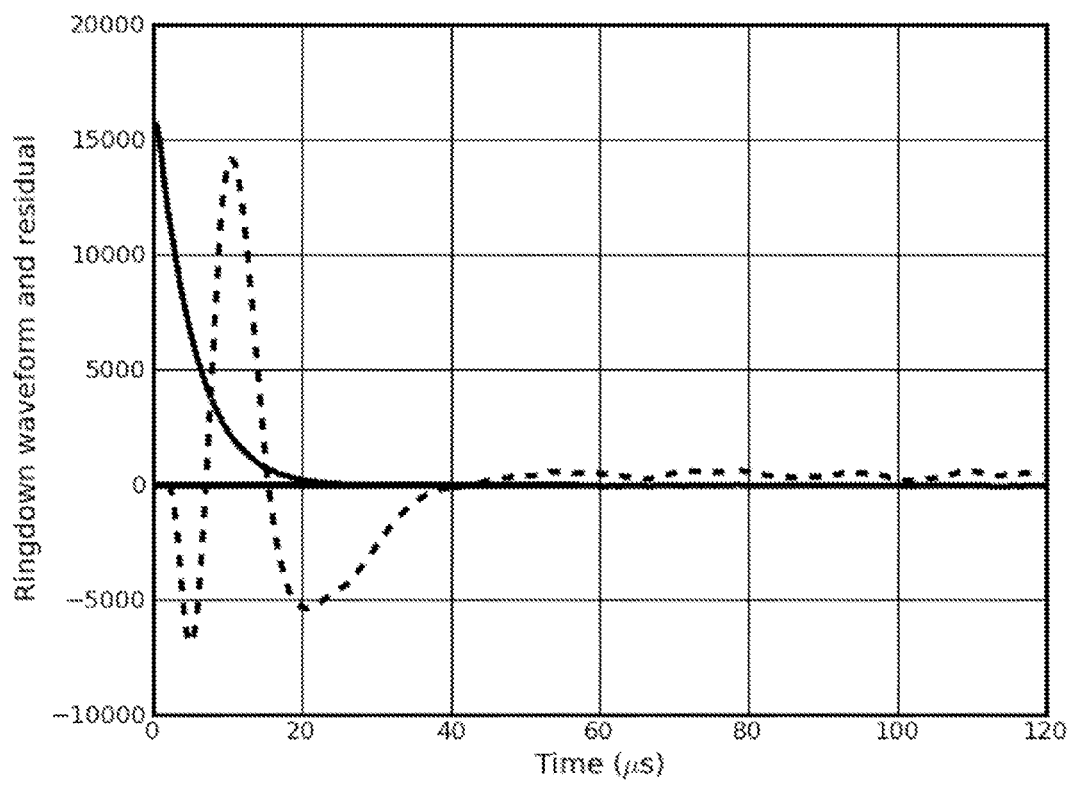
FIG. 6 shows an uncorrected measured ring-down curve and residual (second embodiment).

FIG. 6 shows the detector signal (solid line) of a single ring-down of only the forward output beam. The residual of a pure single-exponential fit multiplied by a factor of 150 is shown with a dashed line.

Figure 7:
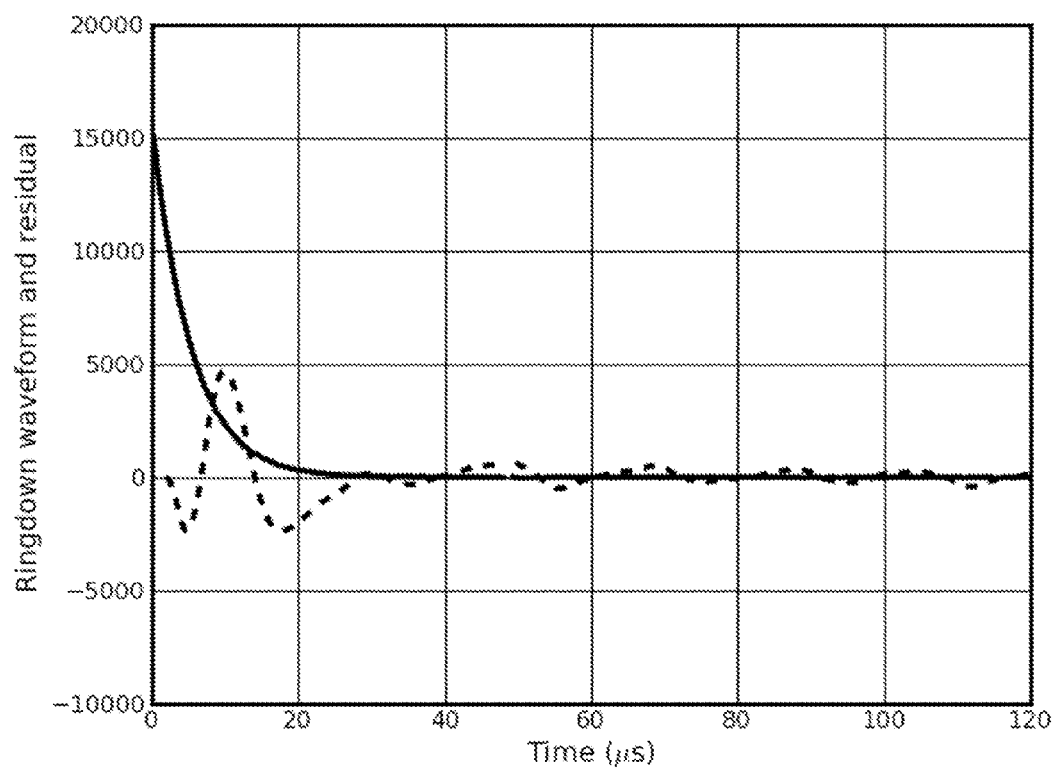
FIG. 7 shows a corrected measured ring-down curve and residual (second embodiment).

FIG. 7 shows the detector signal (solid line) of a single ring-down of forward and backward output beams incident on the same detector (e.g., optical summing). The residual of a pure single-exponential fit multiplied by a factor of 150 is shown with a dashed line. The residual is significantly lower here than on FIG. 6.

Figure 8:
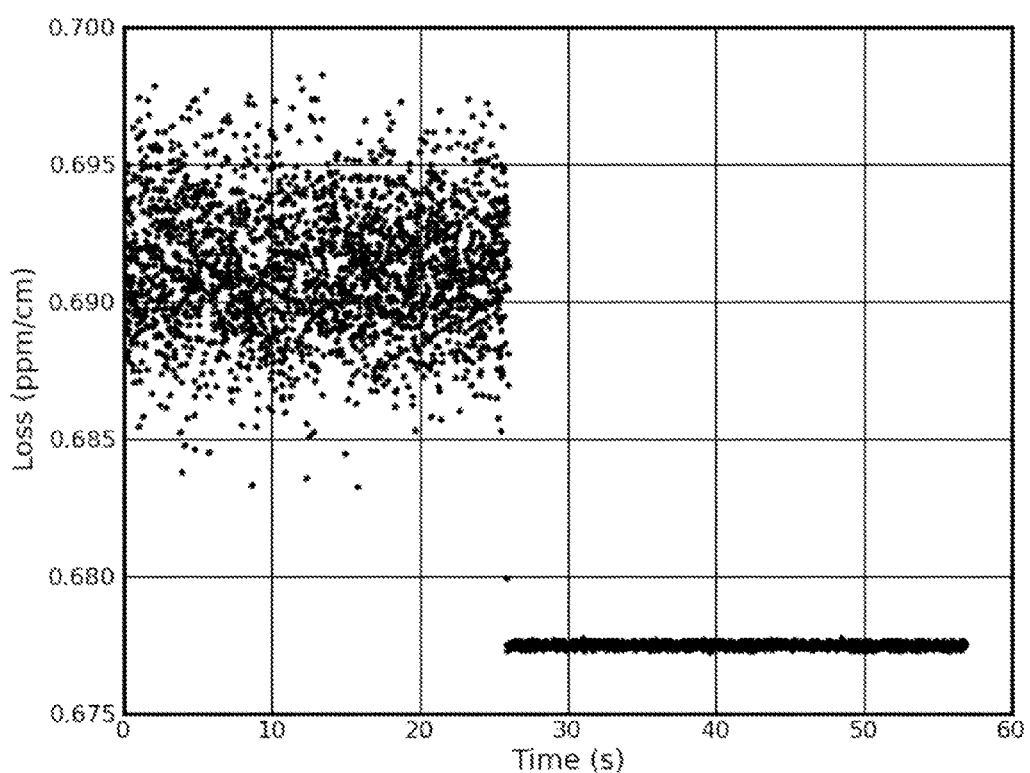
FIG. 8 shows the effect of implementing the correction partway through collecting data for a cavity loss scatter plot (second embodiment).

FIG. 8 shows a time-series of ring-down times. Early times are when only the forward beam is incident on the detector (as in FIG. 6). Later times are when both forward and backward output beams are incident on the ring-down detector (as in FIG. 7). The difference in shot-to-shot variation of the ring-down times is evident.

The preceding description has considered the use of a combined forward and backward mode signal to improve CRDS measurements. It is also possible to analyze the forward and backward mode signals more precisely. In particular, cavity eigenmode signals can be obtained from the forward and backward mode signals. The following description provides an example of this approach in a relatively simple case where the cavity eigenmodes are sine and cosine modes.

In the absence of backscatter coupling, the forward and backward optical waves in the ring-down optical resonator are degenerate: they have identical resonant optical frequencies and ring-down times (at each resonant frequency). When backscatter coupling exists within the ring-down optical resonator, the degeneracy between forward and backward optical waves is broken. In addition, the normal modes of the ring-down resonator are not pure forward and backward traveling waves; they are "sine" and "cosine" standing waves, which are linear combinations of the forward and backward waves. The field amplitudes of these waves transform as:

$$\text{cosine mode} = \frac{1}{\sqrt{2}}[(\text{forward mode})e^{+i\varphi} + (\text{backward mode})e^{-i\varphi}]$$

$$\text{sine mode} = \frac{1}{\sqrt{2}}[(\text{forward mode})e^{+i\varphi} - (\text{backward mode})e^{-i\varphi}]$$

The relative phase, $\varphi$, depends on the physical locations of the point scatterers within the resonator. These sine and cosine normal modes each individually have purely exponential ring-down behavior, and a set of frequency resonances. However, the resonant frequencies and ring-down times are not identical between the modes.

For small backscatter coupling, the resonant frequencies for corresponding mode numbers are slightly shifted from each other and from the degenerate frequency in the absence of coupling. If the real part of the coupling (the power-loss part) is negligible, then the ring-down times are negligibly different, and the power exponential decays are indistinguishable. This is the case mitigated by the two summing methods described above, using either two separate detectors for forward and backward optical beams or directing both beams onto one detector. These methods effectively add the powers of the two normal modes, sine and cosine, together, since the sum of forward and backward waves equals the sum of sine and cosine waves equals the total power circulating within the resonator, as measured by the power emanating from the cavity output mirror.

If the real part of the backscatter coupling (the power-loss part) is not negligible, then the ring-down times of the sine and cosine modes will differ significantly, and the sum of the signals (the total power emanating from the output mirror) will be the sum of two exponential decays, a bi-exponential. Only by observing either normal mode individually will the decay be a pure single exponential. In addition, both ring-down times must be known to extract the effect of the backscatter coupling from other optical losses, such as resonator losses (mirror transmission, or scattering that does not result in backscatter coupling) and analyte absorption and scattering.

Figure 9:
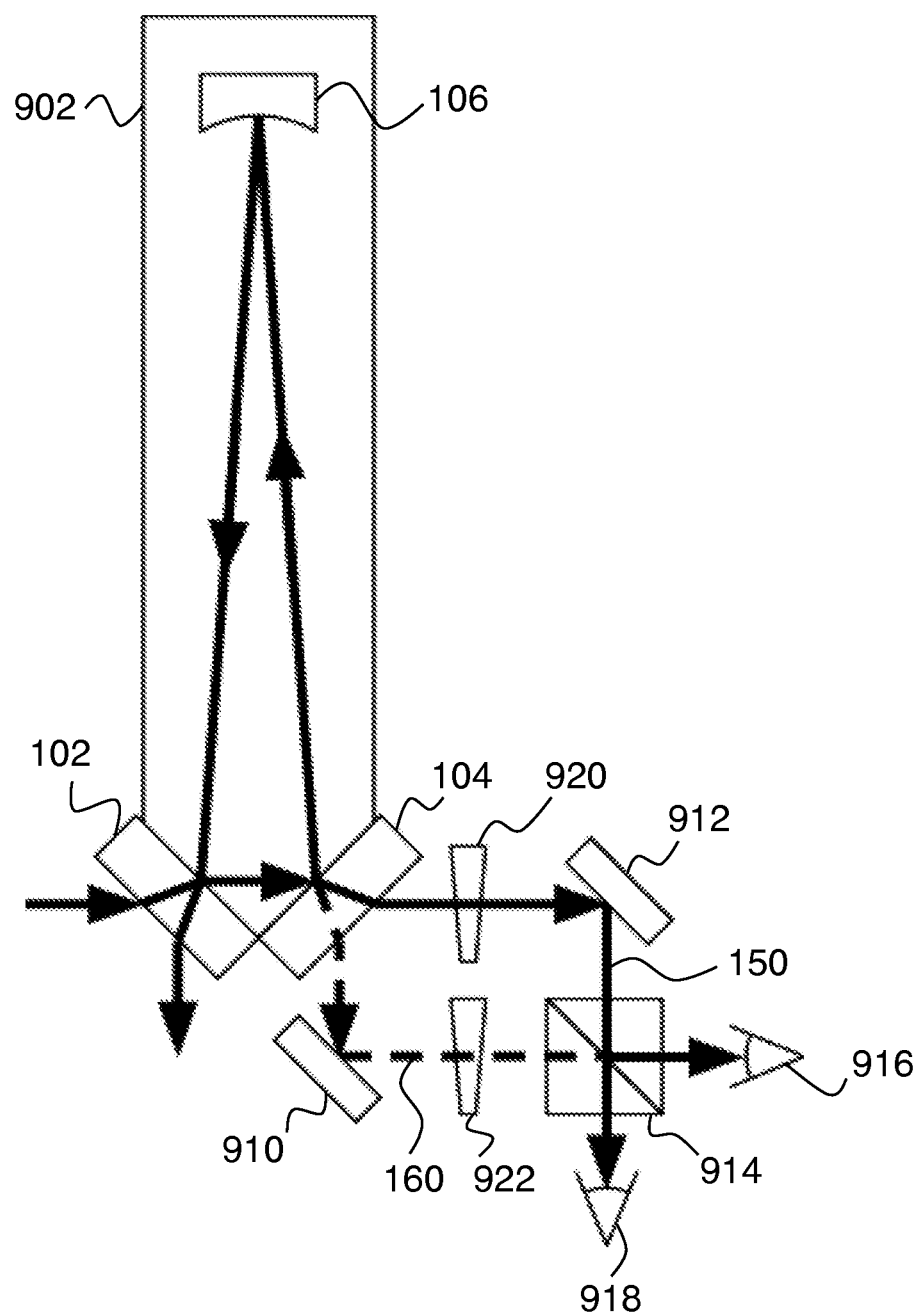
FIG. 9 shows a third embodiment of the invention.

An interferometer, with appropriate optical delay, will transform the forward and backward output beams into the sine and cosine beams. This interferometer can be placed next to the output mirror, as shown in FIG. 9. In this figure, the two output optical beams 150 and 160 from a ring-down cavity 902 are directed along nearly equal paths by mirrors 910 and 912, preferably differing by less than one optical wavelength. The path length difference, $\Delta L$, determines the phase, $\varphi = 2\pi \Delta L/\lambda$. The beam-splitter 914 is preferably 50%/50%. At least one beam from the beam-splitter is directed to a detector 916 (either the sine or cosine beam can be used). The path length difference $\Delta L$ needs to be stable to a small fraction of a wavelength, e.g. a few nm for visible and near-IR. This can be accomplished by attaching the interferometer mirrors 910 and 912 to a stable substrate such as AlN or CuW and controlling the atmosphere, or containing the beams inside a solid prism or prisms. This example includes optional optical wedges 920 and 922 on each beam path to adjust the path lengths independently. Optionally, isolation can be provided by adding isolators (not shown) in the paths of beams 150 and/or 160 between beam splitter 914 and detectors 916 and 918, in a similar manner as described in connection with FIG. 1.

The path length difference $\Delta L$ can be tuned by adjusting the prism(s) or wedge(s) temperature(s) or stress (e.g. with a PZT) or translating the wedges as is one of the typical methods to tune an interferometer of this type. $\Delta L$ should be adjusted to maximize the difference in ring-down decay times observed on the two detectors 916 and 918 (or to an extremum of ring-down time if only one detector is present). By convention, the sine beam has maximum ring-down time and the cosine beam has minimum ring-down time. This is because, in the case of a single point scatterer, the sine wave has a field node (zero field thus minimal interaction) at the location of the scatterer in the resonator, and the cosine wave has an anti-node there (maximum field thus maximum scattering loss). If the scattering properties of the resonator change over time, $\Delta L$ can be readjusted by a feedback loop that continuously or discretely re-maximizes the ring-down time difference (or extremum). The bandwidth over which $\Delta L$ is set properly is approximately $\lambda^2/(r\Delta L)$ where r is the permissible deviation of $(\phi/2\pi)$. If $\Delta L < \lambda_0$ for $\lambda_0$ central wavelength, then the bandwidth essentially extends from $\lambda >> \lambda_0$ to $\lambda \geq \Delta L$.

If the difference in ring-down times between sine and cosine beams is significant, but only the summed beam is observed (either single or dual detector), then the decay signal can be fit to a bi-exponential with either variable or fixed difference between the two decay rates. The fixed difference can be predetermined by characterizing the ring-down either using a temporary interferometer to measure the sine and cosine beams separately, or by carefully fitting the summed signal with a bi-exponential. If the difference between decay times is expected to change slowly, then an averaging loop in the analysis can be used to permit that difference to vary slowly over time, thus partially limiting the degrees of freedom of the fit and reducing its shot-to-shot variability in the short term.

Figure 10:
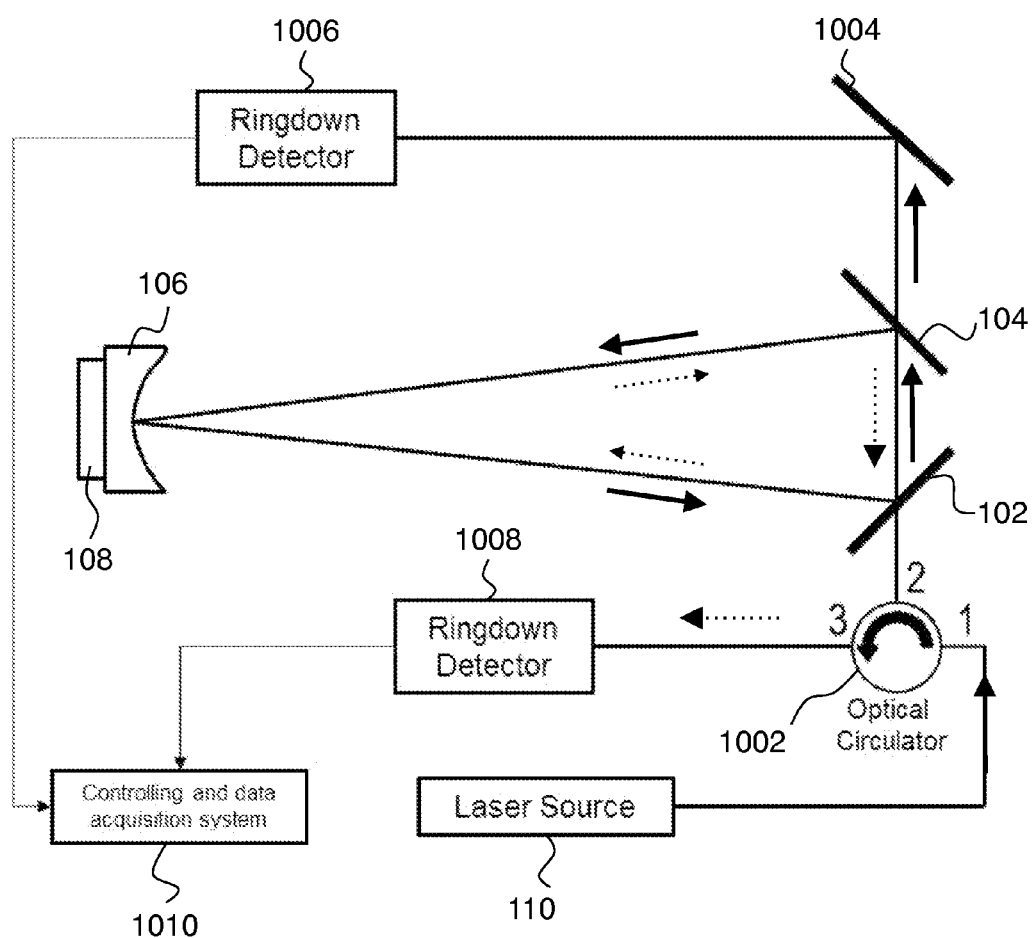
FIG. 10 shows a fourth embodiment of the invention.

FIG. 10 shows an embodiment where an optical circulator is used to facilitate separation of the backward mode signal from the incident source radiation. Here an optical circulator 1002 is present in the system, which has the characteristic behavior that light incident on port 1 is emitted from port 2, and light incident on port 2 is emitted from port 3. Thus light from laser source 110 is incident on mirror 102 of the resonant cavity, and drives the forward propagating mode within the cavity (heavy solid arrows). Forward propagating light emitted from the cavity is received at ringdown detector 1006 (an optional fold mirror 1004 is shown in this example, but has no significant effect on operation).

Within the cavity formed by mirrors 102, 104 and 106, scattering or other processes can lead to the propagation of a backward mode (light dotted arrows). Such backward propagating light will be incident on port 2 of the circulator when it couples out of the resonant cavity, and will therefore be emitted from port 3 of the circular, to be received by ringdown detector 1008. Thus circulator 1002 separates the source radiation from the backward mode signal. Ringdown detectors 1006 and 1008 are connected to control/data acquisition system 1010.

This approach for implementing the back scattered wave correction advantageously eliminates the need for free space optical alignment in the backward beam path. The photocurrents from detectors 1006 and 1008 may be individually amplified and the outputs summed using an analog network or digitally after analog-to-digital conversion. In an alternative realization, these photocurrents may be connected to the summing junction of a single trans-impedance amplifier. It is preferred that the two detection channels be matched as well as possible, and for the outgoing beams to be well-captured by the detectors in order to realize the full benefits of the method.

An optical circulator for separating the source radiation from the backward mode optical signal can also be used in connection with any of the previously described embodiments.

The invention claimed is:

1. Apparatus for performing cavity ring-down spectroscopy (CRDS), the apparatus comprising:
   a traveling-wave cavity having forward and backward optical modes that propagate in opposite directions in the traveling-wave cavity;
   an optical source capable of providing optical source radiation to the optical cavity;
   an optical detection unit that receives a forward mode optical signal from the cavity and a backward mode optical signal from the cavity and provides one or more electrical detector signals derived from the forward mode and backward mode optical signals;
   an optical circulator configured to separate the source radiation from the backward mode optical signal; and
   a processor that receives the electrical detector signals and provides a cavity loss derived from the one or more electrical signals;
   wherein the processor derives a ring-down time from the electrical detector signals and wherein the cavity loss is derived from the ring-down time.

2. The apparatus of claim 1, wherein the optical detection unit comprises two detectors that separately receive the forward mode and backward mode optical signals.

3. The apparatus of claim 1, wherein the optical detection unit comprises a single detector that receives both the forward mode and backward mode optical signals, whereby the single detector provides a sum intensity signal.

4. The apparatus of claim 1, wherein the optical detection unit comprises an optical interferometer capable of transforming the forward mode and backward mode optical signals at an interferometer input to cavity eigenmode optical signals at an interferometer output.

5. The apparatus of claim 1, further comprising an anti-reflection unit disposed between the cavity and the optical detection unit to substantially prevent optical reflections by the optical detection unit from reaching the cavity.

6. The apparatus of claim 5, wherein the anti-reflection unit comprises an optical isolator or a combination of a quarter-wave plate and a linear polarizer.

7. A method for performing cavity ring-down spectroscopy (CRDS), the method comprising:
   providing a traveling-wave cavity having forward and backward optical modes that propagate in opposite directions in the traveling-wave cavity;
   providing optical source radiation to the cavity;
   receiving a forward mode optical signal from the cavity;
   receiving a backward mode optical signal from the cavity;
   providing an optical circulator configured to separate the source radiation from the backward mode optical signal;
   determining a cavity loss from the forward mode and backward mode optical signals; and
   providing the cavity loss as an output;

wherein a ring-down time is derived from the forward mode and backward mode signals and wherein the cavity loss is derived from the ring-down time.

8. The method of claim 7, further comprising deriving a sum intensity signal from the forward mode and backward mode optical signals.

9. The method of claim 8, further comprising performing an exponential fit to the sum intensity signal to determine the cavity loss.

10. The method of claim 8, wherein output signals from two separate detectors are summed to provide the sum intensity signal.

11. The method of claim 10, wherein the output signals from the two detectors are separately amplified and then summed digitally or with analog electronics.

12. The method of claim 10, wherein the output signals from the two detectors are amplified together using a summing amplifier.

13. The method of claim 7, further comprising deriving cavity eigenmode optical signals from the forward mode and backward mode optical signals with an optical interferometer.

14. The method of claim 13, further comprising performing separate exponential fits to the cavity eigenmode optical signals to determine the cavity loss.

15. The method of claim 13, further comprising setting a path length difference of the interferometer to be less than or about equal to a wavelength of an optical source that provides the optical radiation to the cavity.

\* \* \* \* \*